(12) United States Patent
Ota et al.

(10) Patent No.: US 9,826,946 B2
(45) Date of Patent: Nov. 28, 2017

(54) RADIOGRAPHIC APPARATUS WITH X-RAY EMISSION DETECTION

(71) Applicant: Konica Minolta, Inc., Chiyoda-ku, Tokyo (JP)

(72) Inventors: Ikuma Ota, Tokyo (JP); Yoshihiko Eguchi, Tokorozawa (JP); Ryouhei Kikuchi, Hachioji (JP); Tomoya Ogawa, Hachioji (JP)

(73) Assignee: KONICA MINOLTA, INC., Chiyoda-Ku, Tokyo (JP)

( * ) Notice: Subject to any disclaimer, the term of this patent is extended or adjusted under 35 U.S.C. 154(b) by 74 days.

(21) Appl. No.: 14/730,780

(22) Filed: Jun. 4, 2015

(65) Prior Publication Data

US 2015/0351715 A1 Dec. 10, 2015

(30) Foreign Application Priority Data

Jun. 4, 2014 (JP) ................................. 2014-115442

(51) Int. Cl.
*H05G 1/64* (2006.01)
*A61B 6/00* (2006.01)
(Continued)

(52) U.S. Cl.
CPC ............ *A61B 6/4233* (2013.01); *A61B 6/107* (2013.01); *A61B 6/4266* (2013.01);
(Continued)

(58) Field of Classification Search
CPC ........ A61B 6/42; A61B 6/4208; A61B 6/4233
(Continued)

(56) References Cited

U.S. PATENT DOCUMENTS 6,307,915 B1 10/2001 Frojdh
2004/0258204 A1* 12/2004 Nokita ..................... A61B 6/00
378/91
(Continued)

FOREIGN PATENT DOCUMENTS

JP 2008302065 A 12/2008
JP 2008302066 A 12/2008
(Continued)

OTHER PUBLICATIONS

Extended European Search Report corresponding to Application No. 15166426.5-1666/2952136; dated: Mar. 14, 2016.

*Primary Examiner* — Jason McCormack
(74) *Attorney, Agent, or Firm* — Cantor Colburn LLP

(57) ABSTRACT

A radiographic apparatus includes: a plurality of detection elements arranged in a two-dimensional fashion; at least one radiation sensor configured to change a signal value to be output, when radiation is emitted thereto; and an irradiation start detecting unit configured to determine whether X-ray emission from an X-ray generator has been started based on the signal value output from the radiation sensor, wherein, when the signal value output from the radiation sensor moves out of a predetermined range, the irradiation start detecting unit does not determine whether the signal value output from the radiation sensor is a signal value outside the predetermined range at least, and when the number of times the signal value output from the radiation sensor moves out of the predetermined range reaches a predetermined number, the irradiation start detecting unit detects a start of X-ray emission from the X-ray generator.

9 Claims, 9 Drawing Sheets

(51) Int. Cl.
*A61B 6/10* (2006.01)
*H04N 5/32* (2006.01)

(52) U.S. Cl.
CPC .............. *A61B 6/4405* (2013.01); *A61B 6/54* (2013.01); *A61B 6/542* (2013.01); *H04N 5/32* (2013.01); *A61B 6/4283* (2013.01)

(58) Field of Classification Search
USPC ................................ 378/91, 96, 97, 98, 98.8
See application file for complete search history.

(56) References Cited

U.S. PATENT DOCUMENTS

| 2012/0288061 | A1* | 11/2012 | Okada | G01N 23/04 378/62 |
| 2013/0136234 | A1* | 5/2013 | Noma | H05G 1/64 378/91 |
| 2014/0061488 | A1 | 3/2014 | Sato et al. | |

FOREIGN PATENT DOCUMENTS

| JP | 2009219538 A | 10/2009 |
| WO | 9222188 A1 | 12/1992 |

* cited by examiner

RADIOGRAPHIC APPARATUS WITH X-RAY EMISSION DETECTION

CROSS REFERENCE TO RELATED APPLICATIONS

The present invention claims priority under 35 U.S.C. §119 to Japanese Application No. 2014-115442, filed on Jun. 4, 2014, the entire content of which is incorporated herein by reference.

BACKGROUND OF THE INVENTION

Field of the Invention

The present invention relates to a radiographic apparatus, and more particularly, to a radiographic apparatus that includes a radiation sensor.

Description of the Related Art

Radiographic apparatuses that generate charge in detection elements in accordance with a dose of emitted X-rays and read the generated charge as image data are being developed. A radiographic apparatus of this type is known as an FPD (Flat Panel Detector), and is conventionally formed as a special-purpose radiographic apparatus (also called an anchored type, for example) that is integrated with a supporting base or the like. In recent years, however, a radiographic apparatus of a portable type (also called a cassette type, for example) that has detection elements and the like placed in a housing and can be carried around has been developed and put into practical use.

Conventionally, such a radiographic apparatus constructs an interface with an X-ray generator, and exchanges signals and the like with the X-ray generator. When the preparation in the radiographic apparatus is completed, X-rays are emitted from the X-ray generator to the radiographic apparatus via a subject, and imaging is performed. In a case where the radiographic apparatus and the X-ray generator were manufactured by different makers, however, it is not necessarily easy to construct an interface between the two, and an interface cannot be constructed in some cases. If an interface cannot be constructed (or is not constructed) between the radiographic apparatus and the X-ray generator, the problems described below will be caused, for example.

Prior to imaging, a radiographic apparatus normally performs a reset process to remove the remaining charge from the respective detection elements. If there is no interface constructed as described above, the radiographic apparatus continues to perform the reset process on the detection elements, without noticing that X-rays have been emitted from the X-ray generator. As a result, the charge generated in the detection elements through the X-ray emission is removed from the detection elements by the reset process.

If such a situation is caused, the X-ray emission from the X-ray generator is wasted, and the X-ray supply for the X-ray generator is exhausted for nothing. Furthermore, X-rays need to be again emitted from the X-ray generator, and imaging needs to be again performed (retaking). As a result, the patient as the subject is exposed to a larger dose, and further burden is put on the patient.

In view of this, a radiation sensor is attached to a radiographic apparatus, so that the radiographic apparatus detects a start of X-ray emission based on an output value from the radiation sensor. In such a case, when detecting a start of X-ray emission, the radiographic apparatus stops performing the reset process on the detection elements, puts the switching elements of the respective detection elements into an off-sate, and causes the detection elements to transit to a charge accumulating state in which the charge generated in the detection elements through X-ray emission is accumulated in the detection elements.

In a case where a radiation sensor is attached to a radiographic apparatus as described above, however, the radiation sensor senses cosmic rays, and the radiographic apparatus might wrongly detect a start of X-ray emission based on the information about the cosmic rays. In view of this, JP 4881796 B1 discloses a technique by which the position of a radiographic apparatus prior to imaging is adjusted so that the normal line of the detector plane of the radiation sensor attached to the radiographic apparatus extends substantially in the horizontal direction. By this technique, the probability that cosmic rays enter the radiation sensor is reduced.

Meanwhile, a radiographic apparatus disclosed in JP 4763655 B1 compares two or more pieces of image data, and determines whether there is any influence of an external radiation component that is not X-rays emitted from an X-ray generator. If there is some influence, the influence is removed.

In a case where the imaging method disclosed in JP 4881796 B1 is employed, the position of the radiographic apparatus to be used for imaging is limited. A radiographic apparatus of a portable type (a cassette type) can be inserted between the body of a patient and a bed, for example. A radiographic apparatus of a special-purpose type (an anchored type) does not have such an advantageous feature. In a case where a radiographic apparatus of a portable type is used, the normal line of the radiation sensor extends substantially in the vertical line. In a case where a radiographic apparatus of a special-purpose type is used as a radiographic apparatus for so-called recumbent-position imaging, and performs imaging by emitting X-rays from above while the patient is lying on a table, the normal line of the detector plane of the radiation sensor also extends substantially in the vertical line. Where the imaging method disclosed in JP 4881796 B1 is employed, however, the above described imaging with a radiographic apparatus cannot be performed.

In a case where the method disclosed in JP 4763655 B1 is employed, it is only after image data is read out that a check can be made to determine whether there is some influence of an external radiation component. In a case where X-ray emission to a radiographic apparatus is detected based on an output value of a radiation sensor as described above, immediacy is required so as to instantly determine whether the cause of a value output from the radiation sensor is X-ray emission or external radiation, and detect X-ray emission, instead of external radiation. By the method disclosed in JP 4763655 B1, however, it is only after image data is read out that a check can be made to determine whether X-rays are emitted to the radiographic apparatus or whether external radiation is emitted to the radiographic apparatus. This timing is too late.

In the description below, radiation other than X-rays emitted from an X-ray generator, including the cosmic rays disclosed in JP 4881796 B1 and the external radiation disclosed in JP 4763655 B1, will be collectively referred to as natural radiation. Natural radiation includes not only the above mentioned cosmic rays and nature-derived radiation that is emitted from radioactive elements and the like existing in the surface of the ground and under the ground, but also radiation from radiotherapeutic agents and radiotherapeutic test agents existing in facilities such as a hospital, and radiation from radioactive materials derived from artificial nuclear fuel and the like scattered or leaking from a nuclear power plant and the like.

In terms of wavelengths, natural radiation includes not only X-rays but also radiation having wavelengths that exceed the wavelength range of X-rays, such as gamma rays. In this specification, when X-rays emitted from an X-ray generator are not distinguished from natural radiation, any radioactive rays will be referred to simply as radiation.

SUMMARY OF THE INVENTION

The present invention has been made in view of the above circumstances, and an object of the present invention is to provide a radiographic apparatus that does not have any restrictions on its position when performing imaging, distinguishes natural radiation from X-rays emitted from an X-ray generator in real time, detects a start of X-ray emission, and can prevent wrong detection of a start of X-ray emission due to natural radiation.

To achieve the abovementioned object, according to an aspect, a radiographic apparatus reflecting one aspect of the present invention comprises: a plurality of detection elements arranged in a two-dimensional fashion; at least one radiation sensor configured to change a signal value to be output, when radiation is emitted thereto; and an irradiation start detecting unit configured to determine whether X-ray emission from an X-ray generator has been started based on the signal value output from the radiation sensor, wherein, when the signal value output from the radiation sensor moves out of a predetermined range, the irradiation start detecting unit does not determine whether the signal value output from the radiation sensor is a signal value outside the predetermined range at least until a predetermined masking time has passed since the signal value moved out of the predetermined range, and when the number of times the signal value output from the radiation sensor moves out of the predetermined range within a predetermined time since the signal value output from the radiation sensor first moved out of the predetermined range reaches a predetermined number, the irradiation start detecting unit detects a start of X-ray emission from the X-ray generator.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein:

FIG. 6A is a diagram for explaining a masking time and the like;

DESCRIPTION OF THE PREFERRED EMBODIMENTS

Hereinafter, an embodiment of a radiographic apparatus according to the present invention will be described with reference to the drawings. However, the scope of the invention is not limited to the illustrated examples.

In the description below, a so-called indirect radiographic apparatus that includes a scintillator or the like, and obtains electrical signals by converting emitted X-rays into electromagnetic waves of some other wavelength such as visible light will be described as a radiographic apparatus. However, the present invention can be applied to a so-called direct radiography apparatus that directly detects X-rays with detection elements without a scintillator or the like.

Also, a so-called portable radiographic apparatus will be described. However, the present invention can also be applied to a special-purpose radiographic apparatus integrally formed with a support or the like.

[Structure of a Radiographic Apparatus]

Figure 1:
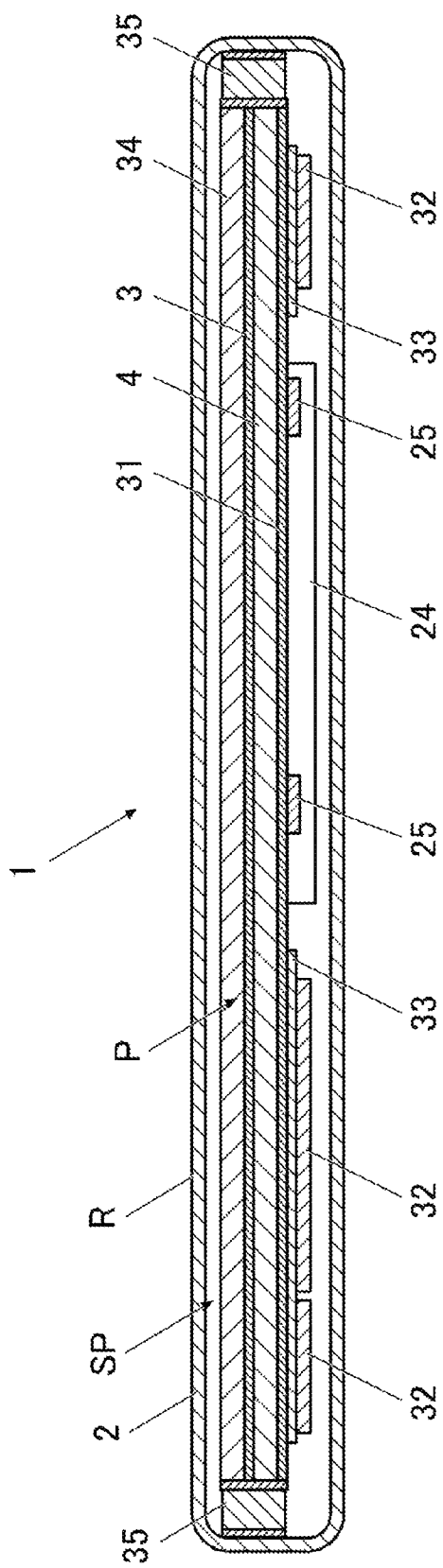
FIG. 1 is a cross-sectional view of a radiographic apparatus.

First, the structure and the like of a radiographic apparatus according to this embodiment are described. FIG. 1 is a cross-sectional view of a radiographic apparatus according to this embodiment. In the description below, the radiographic apparatus 1 will be described based on the vertical and horizontal directions in a case where the radiographic apparatus 1 being placed on a horizontal plane, with the X-ray incidence surface R on the X-ray incidence side facing upward. In the respective drawings, the relative sizes, lengths, and the like of the respective components of the radiographic apparatus 1 do not necessarily reflect the structure of an actual radiographic apparatus.

As shown in FIG. 1, in the radiographic apparatus 1, a sensor panel SP that includes a scintillator 3, a sensor substrate 4, and the like is placed in a housing 2 formed with a carbon plate or the like having the X-ray incidence surface R. A buffer 35 is provided between the sensor panel SP and inner side of the housing 2. Although not shown in FIG. 1, the housing 2 in this embodiment is equipped with an antenna 41 (see 5, which will be described later) that is a wireless communication means to transmit image data D or the like to an image processing device (not shown) in a wireless manner.

Figure 5:
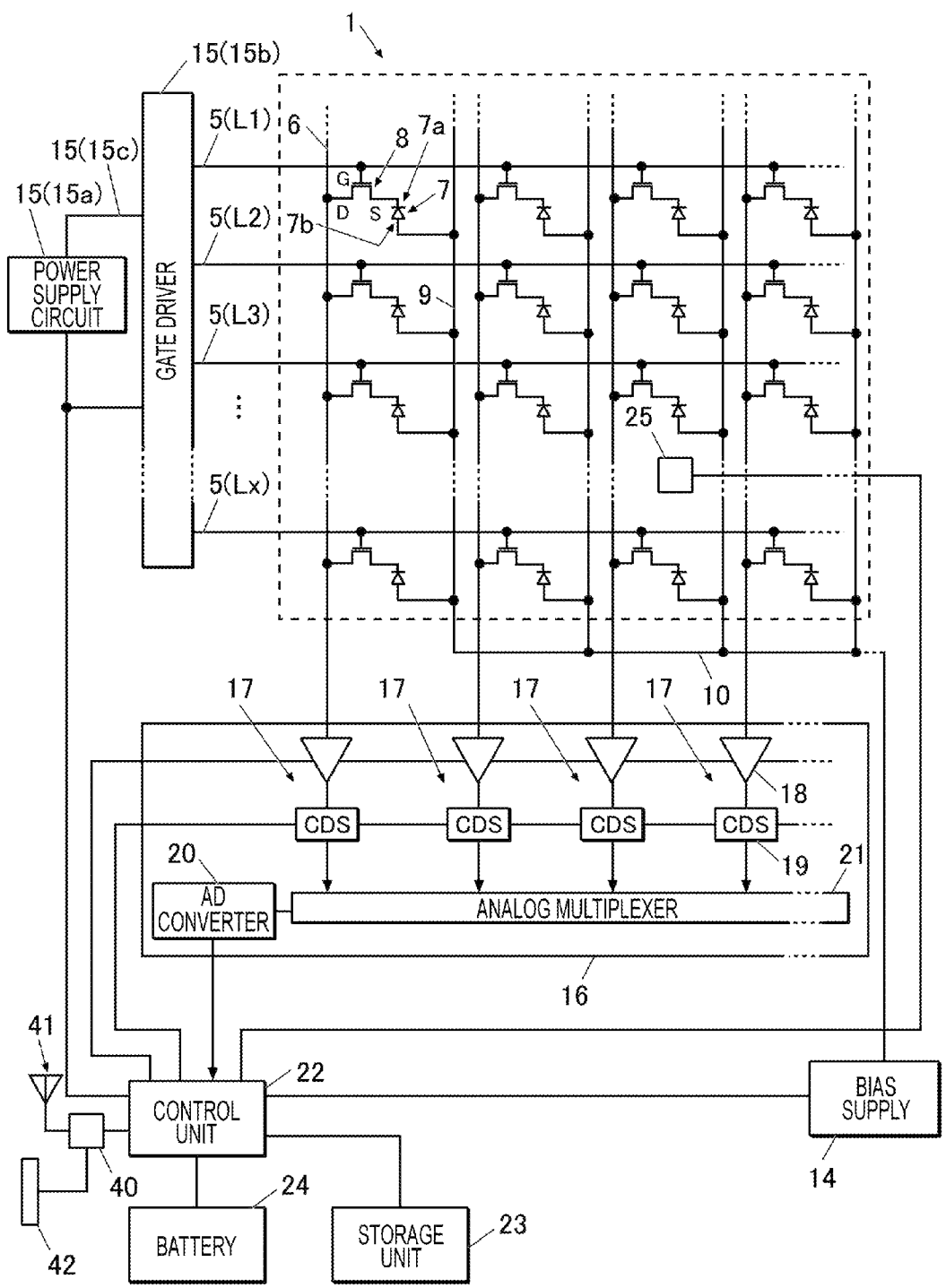
FIG. 5 is a block diagram showing an equivalent circuit of the radiographic apparatus.

Although not shown in FIG. 1, the radiographic apparatus 1 in this embodiment includes a connector 42 (see FIG. 5, which will be described later) on a side surface of the housing 2, and can transmit a signal, data, or the like to a console, an image processing device, or the like (not shown) via the connector 42 in a wired manner. As shown in FIG. 5, which will be described later, a communication unit 40 to which the antenna 41, the connector 42, and the like are connected functions as a communication means for the radiographic apparatus 1.

As shown in FIG. 1, a base 31 is placed in the housing, and the sensor substrate 4 is placed on the X-ray incidence surface R or the upper surface side of the base 31 via a lead thin plate or the like (not shown). On the upper surface side of the sensor substrate 4, the scintillator 3 that converts emitted X-rays into light such as visible light is provided on a scintillator substrate 34, with the scintillator 3 facing toward the sensor substrate 4. PCB substrates 33 having electronic components 32 and the like attached thereto, a battery 24, and the like are provided on the lower surface side of the base 31.

Figure 2:
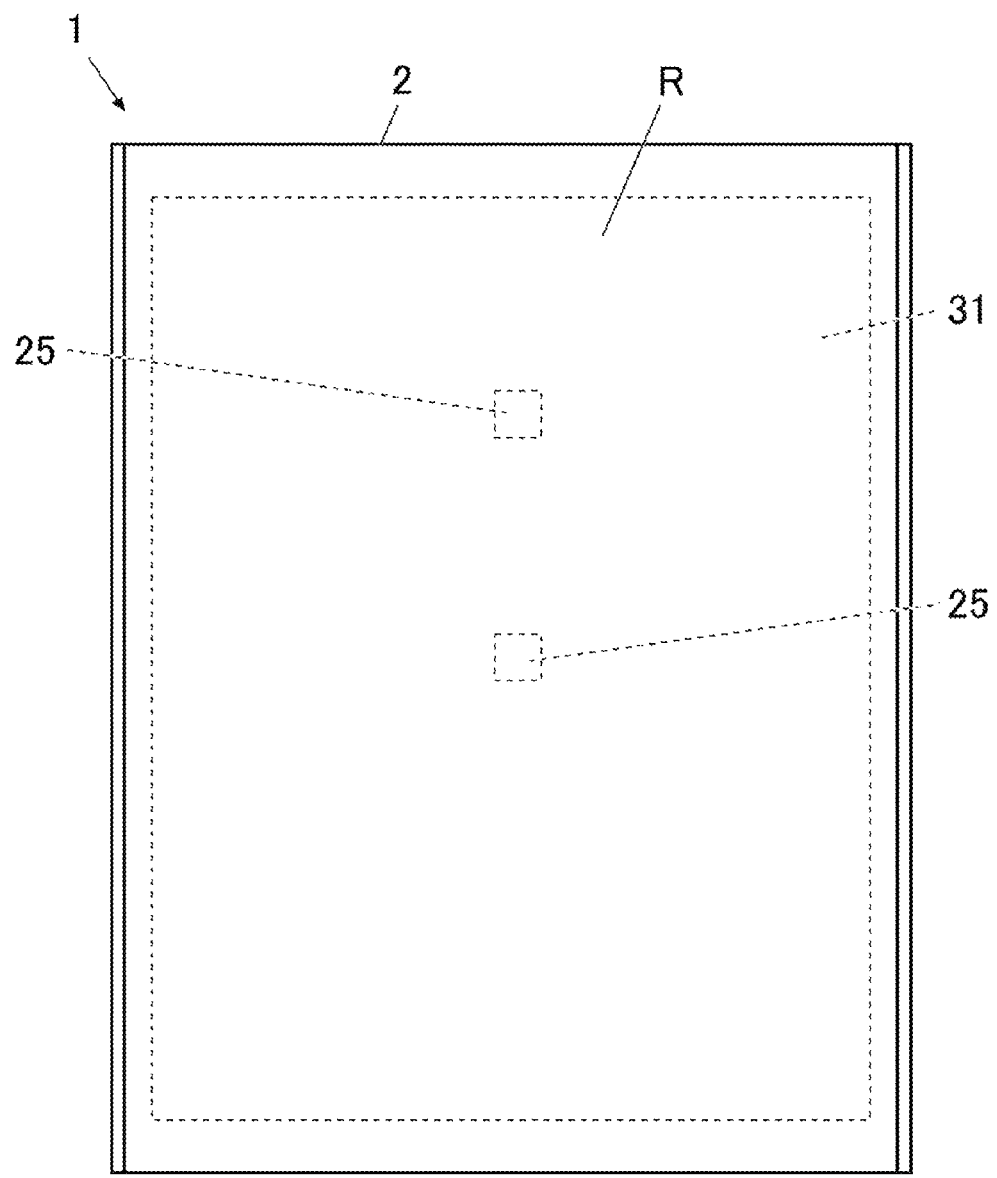
FIG. 2 is a top view of the radiographic apparatus shown in FIG. 1.

Radiation sensors 25 are also attached to the lower surface side of the base 31. In this embodiment, the radiation sensors 25 can sense not only X-rays but also radiation in general. In this embodiment, the radiation sensors 25 are located at the center position and a position other than the center position on the lower surface of the base 31, as shown in FIG. 2. FIG. 2 is a top view of the radiographic apparatus 1, seen from the side of the X-ray incidence surface R or from above.

In this embodiment, the reason that the radiation sensors 25 are placed at the center position on the lower surface of the base 31 and a position other than the center position is as follows. When X-rays are emitted from an X-ray generator to the radiographic apparatus 1, the X-rays are not necessarily emitted to the entire X-ray incidence surface R (see FIGS. 1 and 2), but may be emitted to a narrowed radiation field. In such a case, the radiation field might be narrowed to a position other than the center position on the X-ray incidence surface R of the radiographic apparatus 1.

So as to cope with such a case, a radiation sensor 25 is placed in a position other than the center position on the lower surface of the base 31. Since a radiation sensor 25 is placed in a position other than the center position on the lower surface of the base 31 for the above reason, the radiation sensors 25 can be placed in any appropriate positions, such as at an edge portion or a corner portion of the X-ray incidence surface R of the radiographic apparatus 1, for example, other than placing example as shown in FIG. 2.

There is no need to provide more than one radiographic sensor 25, and it is possible to provide only one radiation sensor 25. Furthermore, the radiation sensors 25 can be attached to the base 31 via the PCB substrates 33 or the like, or may be attached to the inside of the housing 2, though the radiation sensors 25 are attached directly to the base 31 in FIG. 1. That is, the radiation sensors 25 are attached to appropriate portions of the radiographic apparatus 1 in an appropriate manner.

Figure 3:
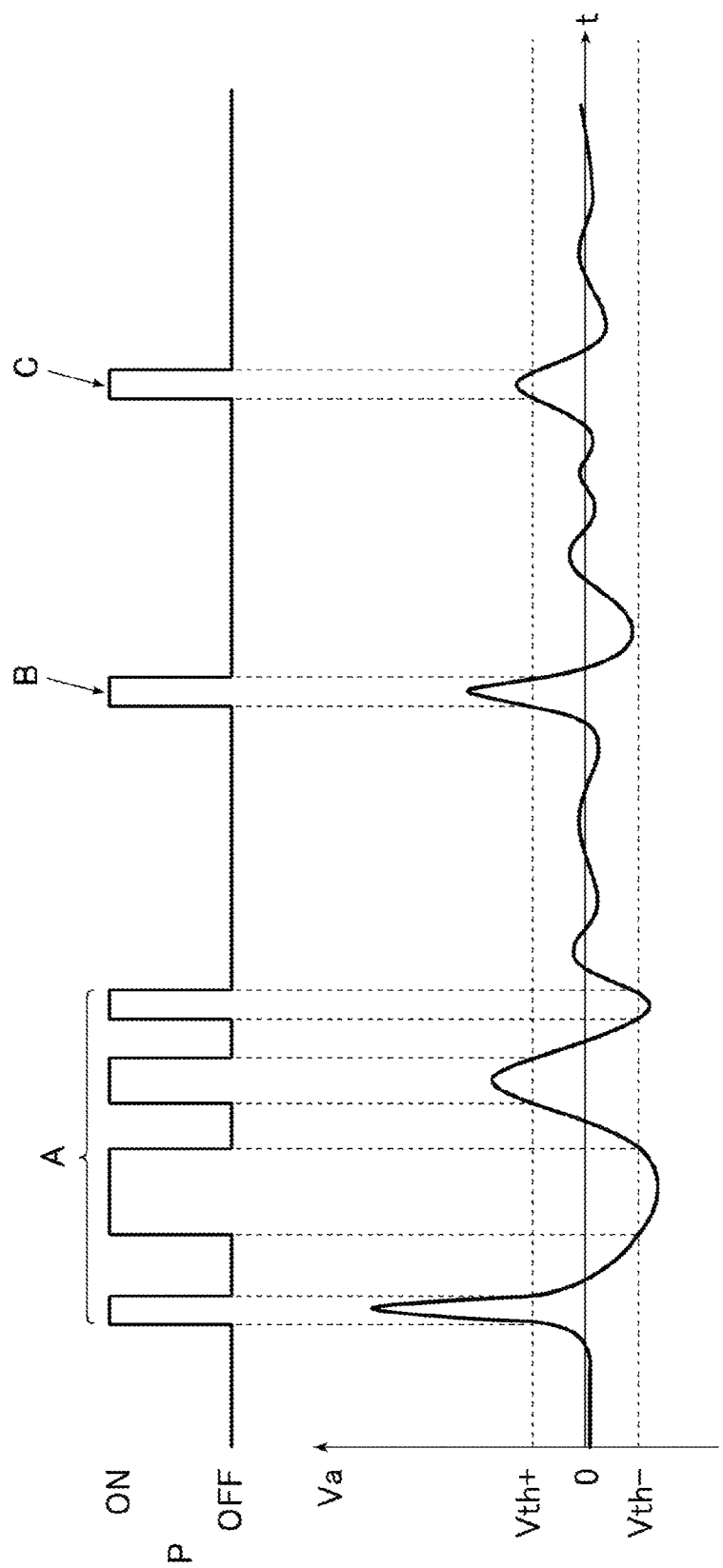
FIG. 3 is a diagram showing an example of a temporal variation in an analog voltage value (the bottom graph) of a radiation sensor of this embodiment, and an example of a pulse signal (the upper graph) to be output in accordance with the analog voltage value.

In this embodiment, the radiation sensors 25 detect not only X-rays emitted from an X-ray generator, but also natural radiation as described above. When detecting emitted X-rays or natural radiation, the radiation sensors 25 change a signal value such as the voltage value to be output. Specifically, when X-rays or the like are emitted to photodiodes or the like (not shown), an ionization effect is caused, and current is applied to the radiation sensors 25. The radiation sensors 25 convert the current into an analog voltage value. In this embodiment, positive and negative threshold values Vth+ and Vth− of the analog voltage value Va are set in the radiation sensors 25, as shown in FIG. 3.

When the analog voltage value Va becomes a voltage value outside the range from the negative threshold value Vth− as the lower limit value to the positive threshold value Vth+ as the upper limit value (such as a voltage value higher than the positive threshold value Vth+, or a voltage value lower than the negative threshold value Vth−), a pulse signal P is output.

It should be noted that A, B, and C shown in FIG. 3 will be described later. In the above described case, the positive and negative threshold values Vth+ and Vth− can be set so as to have the same absolute values, or can be set so as to have different absolute values from each other. Radiation sensors that output the analog voltage value Va as converted from a current value may be used as the radiation sensors 25.

In this embodiment, an X-ray generator that includes an X-ray source such as a Coolidge X-ray source or a rotating anode X-ray source, and is widely used in medical practice is used as the X-ray generator so that X-rays can be emitted to the radiographic apparatus 1. The present invention is not limited to structures that use a specific X-ray generator.

Figure 4:
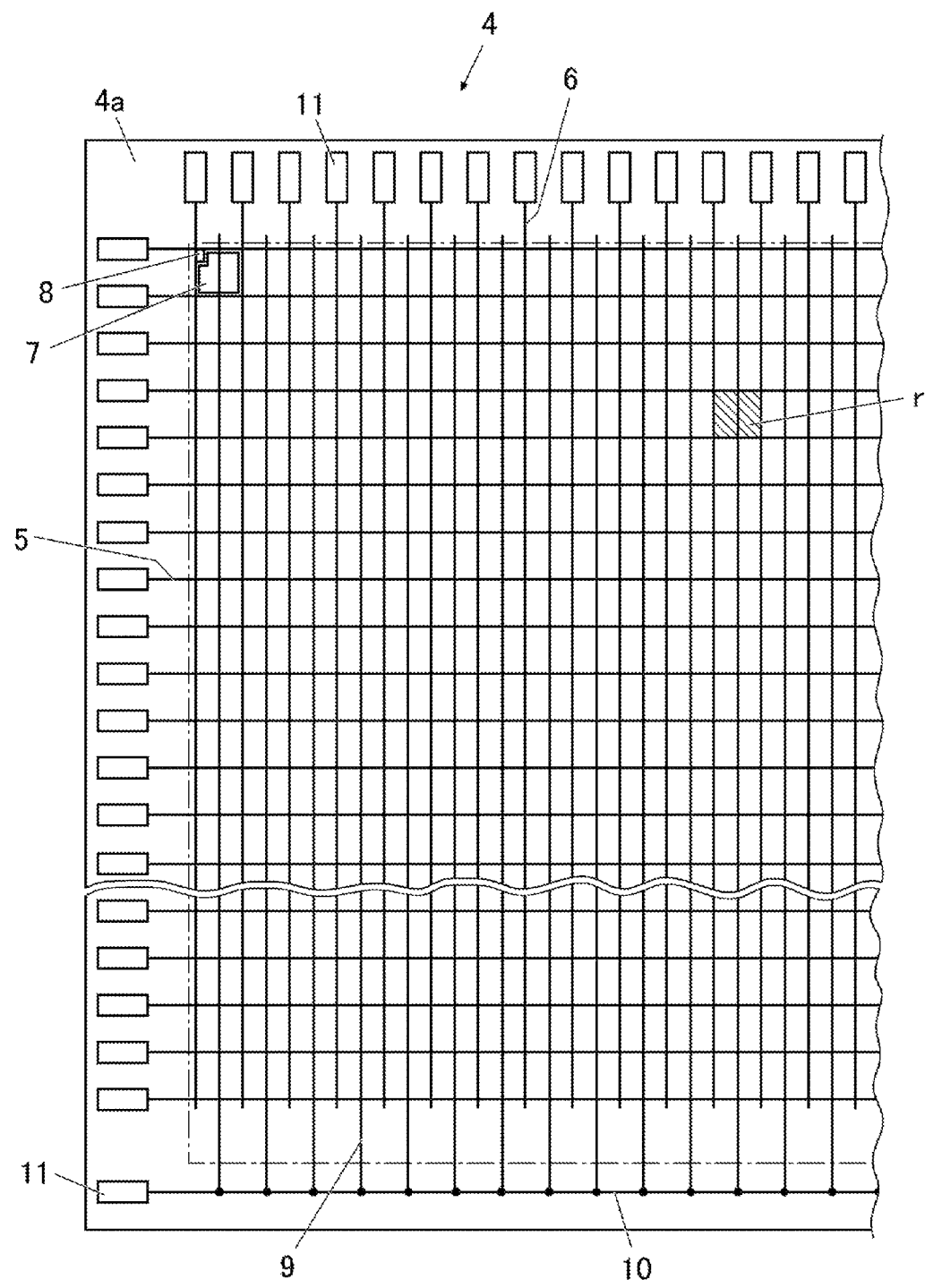
FIG. 4 is a plan view of the structure of the substrate of the radiographic apparatus.

In this embodiment, the sensor substrate 4 is formed with a glass substrate. As shown in FIG. 4, scanning lines 5 and signal lines 6 are provided on the upper surface 4a (the surface facing the scintillator 3) of the sensor substrate 4 so as to cross each other. A detection element 7 is provided in each of the small regions r defined by the scanning lines 5 and the signal lines 6 on the surface 4a of the sensor substrate 4. Although a photodiode is used as each detection element 7 in this embodiment, it is possible to use a phototransistor or a CCD (Charge Coupled Device) instead.

The circuit structure of the radiographic apparatus 1 is now described. FIG. 5 is a block diagram showing an equivalent circuit of the radiographic apparatus 1 according to this embodiment. Although one radiation sensor 25 is shown in FIG. 5, two or more radiation sensors 25 can be provided as mentioned above.

The source electrode 8s (see "S" in FIG. 5) of a thin film transistor (hereinafter referred to as TFT) as a switch element is connected to a first electrode 7a of each detection element 7. The drain electrode 8d and the gate electrode 8g (see "D" and "G" in FIG. 5) of the TFT 8 are connected to a signal line 6 and a scanning line 5, respectively. When an on-state voltage is applied to the gate electrode 8g from a later-described scan drive unit 15 via the scanning line 5, the TFT 8 releases the charge accumulated in the detection element 7 to the signal line 6 via the source electrode 8s and the drain electrode 8d. When an off-state voltage is applied to the gate electrode 8g via the scanning line 5, the TFT 8 enters an off-state, stops the charge release from the detection element 7 to the signal line 6, and accumulates charge in the detection element 7.

As shown in FIGS. 4 and 5, in this embodiment, a bias line 9 is connected to the second electrodes 7b of the respective detection elements 7 in each one column on the sensor substrate 4, and the respective bias lines 9 are bound together by a connecting line 10 at an edge portion of the sensor substrate 4. The connecting line 10 is connected to a bias supply 14 (see FIG. 5) via an input/output terminal 11 (also called a pad; shown in FIG. 4), so that a reverse bias voltage is applied from the bias supply 14 to the second electrodes 7b of the respective detection elements 7 via the connecting line 10 and the respective bias lines 9.

Meanwhile, the respective scanning lines 5 are connected to a gate driver 15b of the scan drive unit 15 via input/output terminals 11. In the scan drive unit 15, an on-state voltage and an off-state voltage are supplied from a power supply circuit 15a to the gate driver 15b via an interconnect 15c, and the voltage to be applied to the respective lines L1 through Lx of the scanning lines 5 is switched between the on-state voltage and the off-state voltage by the gate driver 15*b*.

The respective signal lines 6 are connected to respective readout circuits 17 included in a readout IC 16 via the respective input/output terminals 11. In this embodiment, each readout circuit 17 is formed mainly with an amplifier circuit 18 and a correlated double sampling circuit 19. Although not shown in the drawing, each amplifier circuit 18 in this embodiment is formed with a charge amplifier circuit that includes an operational amplifier and a capacitor or the like connected in parallel, and a voltage value that corresponds to the quantity of charge accumulated in the capacitor is output from the output side of the operational amplifier to the correlated double sampling circuit 19 (see CDS in FIG. 5). As shown in FIG. 5, an analog multiplexer 21 and an AD converter 20 are further provided in the readout IC 16.

When image data D is read from each detection element 7, the on-state voltage is applied from the gate driver 15*b* of the scan drive unit 15 to a scanning line 5, and the respective corresponding TFTs 8 are put into an on-state. Charge is then released from the respective detection elements 7 to the signal lines 6 via the respective TFTs 8, and is accumulated in the capacitors of the amplifier circuits 18 in the readout circuits 17. As described above, in the amplifier circuit 18 of each readout circuit 17, the voltage value that corresponds to the quantity of charge accumulated in the capacitor is output from the operational amplifier to the correlated double sampling circuit 19.

Each correlated double sampling circuits 19 outputs image data D that is the analog value of the increase that is caused in the value output from the corresponding amplifier circuit 18 when the charge flows from the corresponding detection element 7 into the amplifier circuit 18. The image data D is output to the downstream side. The respective pieces of the output image data D are sequentially transmitted to the AD converter 20 via the analog multiplexer 21, and are sequentially converted into digital image data D by the AD converter 20. The digital image data D is output to the storage unit 23, and is sequentially stored therein. In this manner, the image data D is read out.

A control unit 22 is formed with a computer (not shown) that includes a CPU (Central Processing Unit), a ROM (Read Only Memory), a RAM (Random Access Memory), an input/output interface, and the like, which are connected to a bus, or an FPGA (Field Programmable Gate Array) (not shown), for example. Alternatively, the control unit 22 may be formed with a special-purpose control circuit. The control unit 22 controls operations of the respective functional units of the radiographic apparatus 1, such as causing the scan drive unit 15 and the readout circuit 17 to read out the image data D in the above described manner.

As shown in FIG. 5, a storage unit 23 that is formed with an SRAM (Static RAM) or an SDRAM (Synchronous DRAM) is connected to the control unit 22. In this embodiment, the communication unit 40 to which the antenna 41 and the connector 42 described above are connected is also connected to the control unit 22. Further, the battery 24 that supplies necessary power to the respective functional units such as the scan drive unit 15, the readout circuit 17, the storage unit 23, and the bias supply 14, is connected to the control unit 22.

Although the control unit 22 also functions as the irradiation start detecting unit of the radiographic apparatus 1, which will be described later, the irradiation start detecting unit can be provided as a unit that is independent of the control unit 22. In the description below, in a case where the control unit 22 functions as the irradiation start detecting unit, the control unit 22 will be referred to as the irradiation start detecting unit 22. As shown in FIG. 5, the above described radiation sensor 25 is connected to the irradiation start detecting unit 22 (the control unit 22), so that signals that are output from the radiation sensor 25 are input to the irradiation start detecting unit 22.

[Structure and the Like Unique to the Present Invention]

The following is a description of a structure and the like that are unique to the present invention for enabling accurate detection of a start of X-ray emission from the X-ray generator, not a start of delivery of natural radiation, in a situation where natural radiation might be detected. The operation of the radiographic apparatus 1 according to this embodiment is also described below.

In the description below, each of the radiation sensors 25, as shown in FIG. 3, is a radiation sensor that is designed to output a pulse signal P (that is ON in FIG. 3) when the analog voltage value Va as the signal value to be output is outside a predetermined range (or the range defined by the positive threshold value Vth+ as the upper limit value and the negative threshold value Vth− as the lower limit value in the case shown in FIG. 3). The irradiation start detecting unit 22 determines whether X-ray emission from the X-ray generator has been started based on the pulse signal P transmitted from the radiation sensor 25.

Alternatively, the analog voltage value Va as the signal value may be output from the radiation sensor 25 to the irradiation start detecting unit 22, and the irradiation start detecting unit 22 may determine whether the voltage value Va as the signal value to be output from the radiation sensor 25 is outside the predetermined range, and, in accordance with a result of the determination, determine whether X-ray emission from the X-ray generator has been started. The present invention can also be applied in such a case.

Although operation in such a structures will not be described, as shown in FIG. 3, the periods during which the voltage value Va output from the radiation sensor 25 is outside the predetermined range correspond to the periods during which the pulse signal P is output (or the period during which the pulse signal is ON in FIG. 3) in the description below. Accordingly, a case where the analog voltage value Va, instead of the pulse signal P, is output from the radiation sensor 25 to the irradiation start detecting unit 22 can also be described as below by replacing the periods during which the pulse signal P is output with the periods during which the voltage value Va output from the radiation sensor 25 is outside the predetermined range in the description below.

[Basic Structure in a Detection Process Unique to the Present Invention]

When radiation is emitted from the X-ray generator to the radiographic apparatus 1 via a subject (not shown), X-rays reach the radiation sensor 25 provided in the radiographic apparatus 1, and a photodiode or the like (not shown) in the radiation sensor 25 is irradiated with the X-rays. An ionization effect is then caused to apply current, and the current is converted into the analog voltage value Va, as described above. When the analog voltage value Va is outside a predetermined range, or is outside the range defined by the positive threshold value Vth+ as the upper limit value and the negative threshold value Vth− as the lower limit value in this embodiment, the pulse signal P is output from the radiation sensor 25.

In that case, even if X-rays are emitted from the X-ray generator at a fixed dose rate, the phenomenon that the photons that constitute the X-rays reach the radiation sensor 25 is a probabilistic phenomenon. Therefore, in a case where X-rays are emitted from the X-ray generator to the radiographic apparatus 1, the pulse signal P is randomly output from the radiation sensor 25 provided in the radiographic apparatus 1. As long as X-rays are emitted from the X-ray generator to the radiographic apparatus 1, the pulse signal P continues to be randomly output from the radiation sensor 25.

In a case where natural radiation reaches the radiation sensor 25, the pulse signal P is also output from the radiation sensor 25, but natural radiation normally reaches the radiation sensor 25 only once. To be more precise, the frequency at which natural radiation reaches the radiation sensor 25 is lower than the frequency at which X-rays reach the radiation sensor 25 in a case where X-rays are emitted from the X-ray generator to the radiographic apparatus 1. In other words, the period of time required for natural radiation to reach the radiation sensor 25 is normally much longer than the period of time required for X-rays to reach the radiation sensor 25 in a case where X-rays are emitted from the X-ray generator to the radiographic apparatus 1.

Therefore, when the pulse signal P being output from the radiation sensor 25 is monitored for a predetermined time $\Delta T$ since radiation reached the radiation sensor 25 and the radiation sensor 25 started outputting the pulse signal P, the pulse signal P is output several times during the predetermined time T in a case where the radiation that has reached the radiation sensor 25 is X-rays generated from the X-ray generator. In a case where the radiation that has reached the radiation sensor 25 is natural radiation, on the other hand, the probability that the pulse signal P is output for the second time during the predetermined time $\Delta T$ is very low, and there is almost no probability that the pulse signal P is output for the third time during the predetermined time $\Delta T$.

In view of this, the irradiation start detecting unit 22 in this embodiment is designed to monitor the pulse signal P being output from the radiation sensor 25, and determine that X-ray emission from the X-ray generator has been started when the number of times the pulse signal P is output from the radiation sensor 25 within the predetermined time T since the radiation sensor 25 started outputting the pulse signal P (or the number of times the voltage value Va as the signal value output from the radiation sensor 25 is outside the predetermined range) reaches a predetermined number N. The setting of the predetermined time $\Delta T$ and the predetermined number N will be described later.

If the irradiation start detecting unit 22 is designed to instantly determine that X-ray emission from the X-ray generator has been started when the pulse signal P is output from the radiation sensor 25, the irradiation start detecting unit 22 also determines that X-ray emission from the X-ray generator has been started when the pulse signal P is output from the radiation sensor 25 because natural radiation has reached the radiation sensor 25. As a result, a start of X-ray detection is wrongly detected. However, in a case where a start of X-ray emission is detected only after the pulse signal P is output from the radiation sensor 25 the predetermined number N of times as described above, wrong detection can be certainly prevented.

In a case where the irradiation start detecting unit 22 is designed to determine that X-ray emission from the X-ray generator has been started when the pulse signal P has been output from the radiation sensor 25 the predetermined number N of times, natural radiation reaches the radiation sensor 25 the predetermined number N of times in a long period of time. As a result, a start of X-ray emission is wrongly detected at that time. Therefore, the number of times the pulse signal P is output from the radiation sensor 25 during the predetermined time $\Delta T$ since the radiation sensor 25 started outputting the pulse signal P is counted as described above, and the predetermined number N of times is set at such a number that natural radiation is not detected within the predetermined time $\Delta T$. Accordingly, wrong detection can be appropriated prevented.

In view of this, the irradiation start detecting unit 22 is designed to determine that X-ray emission from the X-ray generator has been started only when the number of times the pulse signal P has been output from the radiation sensor 25 reaches the predetermined number N within the predetermined time $\Delta T$ since the radiation sensor 25 started outputting the pulse signal P. Accordingly, a start of X-ray emission from the X-ray generator can be detected with precision, and wrong detection of natural radiation as a start of X-ray emission can be certainly prevented.

[Phenomenon that Occurs when Natural Radiation Reaches the Radiation Sensor]

Next, a unique phenomenon that occurs when natural radiation reaches the radiation sensor 25, and the measure to be taken to cope with the phenomenon are described.

In general, natural radiation characteristically has greater energy than X-rays emitted from an X-ray generator. Therefore, when natural radiation enters the radiation sensor 25, the waveform of the voltage value Va changes greatly like the analog voltage value Va corresponding to the pulse signal P indicated by A in FIG. 3, for example. When natural radiation enters the radiation sensor 25, the voltage value Va becomes larger than the positive threshold value Vth+, and the pulse signal P is output accordingly. After that, the voltage value Va becomes lower than the negative threshold value Vth−, and the pulse signal P is again output. Further, the voltage value Va again becomes higher than the positive threshold value Vth+, and the pulse signal P is output. This phenomenon continues thereafter. Therefore, in many cases, the pulse signal P is output more than once when natural radiation enters the radiation sensor 25 once.

In a case where X-rays emitted from the X-ray generator enter the radiation sensor 25, on the other hand, the voltage value Va momentarily becomes greater than the positive threshold value Vth+ when the X-rays enter the radiation sensor 25, like the analog voltage values Va corresponding to the pulse signals P indicated by B and C in FIG. 3, for example. As a result, the pulse signal P is output. After that, even if the voltage value Va changes greatly, the voltage value Va neither becomes lower than the negative threshold value Vth− nor becomes higher than the positive threshold value Vth+ again. Therefore, when X-rays enter the radiation sensor 25 once, the pulse signal P is normally output only once. However, if X-rays emitted from the X-ray generator have great energy, the pulse signal P might be output more than once after the X-rays enter the radiation sensor 25, as in the case of the natural radiation indicated by A in FIG. 3.

In such a case, if the irradiation start detecting unit 22 is designed to determine that X-ray emission from the X-ray generator has been started when the pulse signal P has been output the predetermined number N of times within the predetermined time $\Delta T$ since the radiation sensor 25 started outputting the pulse signal P, the irradiation start detecting unit 22 wrongly detect a start of X-ray emission from the X-ray generator when the pulse signal P has been output from the radiation sensor 25 the predetermined number N of times or more, even though natural radiation with large energy has reached the radiation sensor 25 only once.

Specifically, in a case where the irradiation start detecting unit 22 is designed to determine that X-ray emission has been started when the pulse signal P has been output three times, with three being the predetermined number N, the irradiation start detecting unit 22 wrongly detects a start of X-ray emission from the X-ray generator when the pulse signal P has been output three or more times (four times, including the first pulse signal P, in the case of A in FIG. 3) within the predetermined time ΔT (not shown in FIG. 3) since natural radiation reached the radiation sensor 25 and the first pulse signal P was output, as indicated by A in FIG. 3, for example. In this manner, a start of X-ray emission is wrongly detected, even though it is natural radiation that reached the radiation sensor 25, and X-rays have not been emitted from the X-ray generator.

So as to prevent such wrong detection, the irradiation start detecting unit 22 in this embodiment is designed not to determine whether the pulse signal P has been output from the radiation sensor 25 at least before a predetermined masking time Δtm has passed since the radiation sensor 25 started outputting the pulse signal P.

Even when the pulse signal P is output from the radiation sensor 25, the irradiation start detecting unit 22 designed as described above substantially ignores the pulse signal P before the predetermined masking time Δtm has passed since the radiation sensor 25 started outputting the pulse signal P. Accordingly, even when the radiation sensor 25 outputs the pulse signal P a few more times within the masking time Δtm after outputting the pulse signal P for the first time, the irradiation start detecting unit 22 detects the pulse signal P output from the radiation sensor 25 only once, as shown in FIG. 6A, for example.

Figure 6A:
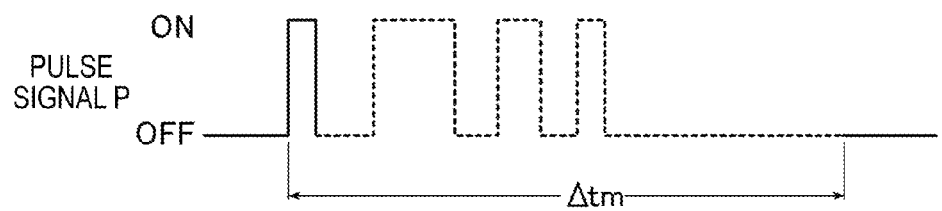
Figure 6B:
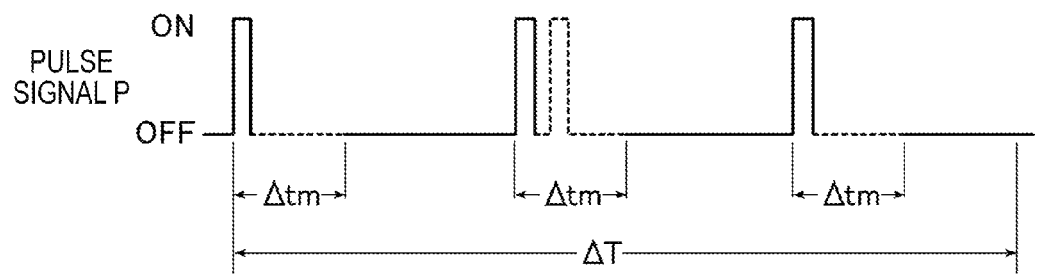
FIG. 6B is a diagram for explaining the counting of the number of times a pulse signal P is output in a case where the masking time is set.

As shown in FIG. 6B, for example, the irradiation start detecting unit 22 in this embodiment is designed to determine that X-ray emission from the X-ray generator has been started when the pulse signal P has been output the predetermined number N of times (three times in the case shown in FIG. 6B) within the predetermined time ΔT since the radiation sensor 25 started outputting the pulse signal P as described above, with the masking time Δtm putting limitations as described above.

With this structure, the irradiation start detecting unit 22 detects only the pulse signal P that is first output and ignores the pulse signal P that is output thereafter within the masking time Δtm as shown in FIG. 6A, though the pulse signal P is output from the radiation sensor 25 more than once in a case where natural radiation enters the radiation sensor 25. Accordingly, the irradiation start detecting unit 22 determines that the pulse signal P has been output from the radiation sensor 25 only once. Where the radiation that has entered the radiation sensor 25 is natural radiation, the pulse signal P is not output after the masking time Δtm has passed (or the probability that the pulse signal P is output three times at least within the predetermined time ΔT is almost zero). Accordingly, a start of X-ray emission from the X-ray generator is not wrongly detected.

As described above, when natural radiation enters (reaches) the radiation sensor 25, the irradiation start detecting unit 22 can be certainly prevented from wrongly detecting a start of X-ray emission from the X-ray generator.

In a case where X-rays emitted from the X-ray generator reach the radiation sensor 25, even if the masking time Δtm is set as described above, the pulse signal P continues to be output from the radiation sensor 25 as shown in FIG. 6B, as long as X-rays are being emitted from the X-ray generator.

Accordingly, the irradiation start detecting unit 22 can detect that the pulse signal P has been output the predetermined number N of times (three times in FIG. 6B) within the predetermined time ΔT since the radiation sensor 25 output the pulse signal P for the first time. Thus, the irradiation start detecting unit 22 can precisely detect a start of X-ray emission from the X-ray generator, even if the masking time Δtm is set as described above.

[Processes Before and after Detection of a Start of X-Ray Emission]

The control unit 22 of the radiographic apparatus 1 sequentially or collectively applies the on-state voltage from the gate driver 15b (see FIG. 5) of the scan drive unit 15 to the respective lines L1 through Lx of the scanning lines 5 prior to imaging (or before X-ray emission from the X-ray generator is started), to put the respective TFTs 8 into an on-state. The control unit 22 then performs a reset process on the respective detection elements 7, to remove the charge remaining in the respective detection elements 7, so-called dark charge (or also called dark current) generated in the respective detection elements 7, and the like.

In this embodiment, the control unit 22 as the irradiation start detecting unit performs a detection process in the above described manner. When determining that X-ray emission from the X-ray generator has been started, the control unit 22 applies the off-state voltage to the respective lines L1 through Lx of the scanning lines 5 from the gate driver 15b, to put the respective TFTs 8 into an off-state. The charge generated in the detection elements 7 through the exposure to X-rays is then accumulated in the detection elements 7. This state is called a charge accumulating state. After the exposure to X-rays is ended, the on-voltage is sequentially applied from the gate driver 15b to the respective lines L1 through Lx of the scanning lines 5, so that the image data D is read out from the respective detection elements 7 in the above described manner.

After a start of X-ray emission is detected, the pulse signal P being output from the radiation sensor 25 can be monitored, for example, and an end of X-ray emission from the X-ray generator may be detected when the outputting of the pulse signal P from the radiation sensor 25 is stopped. Before or after imaging, known processes are performed, such as a process of reading out offset data O, or transmitting the image data D, the offset data O, and the like from the radiographic apparatus 1 to an image processing device (not shown).

[Effects]

As described above, in the radiographic apparatus 1 according to this embodiment, the irradiation start detecting unit 22 is designed not to determine whether the pulse signal P has been output from the radiation sensor 25 at least before the predetermined masking time Δtm has passed since the radiation sensor 25 started outputting the pulse signal P. Under this condition, the irradiation start detecting unit 22 determines that X-ray emission from the X-ray generator has been started only after the pulse signal P has been output from the radiation sensor 25 the predetermined number N of times within the predetermined time ΔT.

Accordingly, a start of X-ray emission from the X-ray generator can be precisely detected as described above, and wrong detection of a start of X-ray emission when natural radiation enters the radiation sensor 25 can be certainly prevented.

Where the masking time Δtm (see FIGS. 6A and 6B) is set at several hundreds of microseconds, and the predetermined time ΔT is set at a value on the order of milliseconds, for example, X-ray emission from the X-ray generator can be detected in a time on the order of milliseconds, and a start of X-ray emission from the X-ray generator can be detected in real time. Accordingly, when X-ray emission from the X-ray generator is started, the TFTs 8 are instantly put into an off-state, and the charge accumulating state starts. The charge generated in the respective detection elements 7 through X-ray emission can be accumulated in the respective detection elements 7, and a radiological image can be precisely taken and generated.

In the radiographic apparatus 1 according to this embodiment, even when natural radiation such as cosmic rays enter the radiation sensor 25, wrong detection of a start of X-ray emission from the X-ray generator can be certainly prevented. Accordingly, imaging can be performed with the radiographic apparatus 1, without the need to adjust the radiographic apparatus 1 so that the normal line of the detector plane of the radiation sensor 25 attached to the radiographic apparatus 1 extends substantially in the horizontal direction as disclosed in JP 4881796 B1. Thus, a radiographic apparatus 1 of a portable time (a cassette type) can be inserted between the body of a patient and a bed when imaging is performed. In this manner, the advantageous features of the radiographic apparatus 1 of a portable type can be fully used in imaging. Also, with a radiographic apparatus 1 specially designed for recumbent-position imaging, accurate imaging can be performed, without being affected by natural radiation such as cosmic rays.

[Modifications of the Process of Detecting a Start of X-Ray Emission]

Next, modifications of the process of detecting a start of X-ray emission from the X-ray generator in the radiographic apparatus according to this embodiment are described through various specific examples.

[Modification 1]

As described above, the radiographic apparatus 1 is expected to achieve the following two purposes: (1) to prevent wrong detection of a start of X-ray emission due to natural radiation; and (2) to promptly detect X-ray emission from the X-ray generator, and enter the charge accumulating state to precisely accumulate the charge generated in the detection elements 7 through the X-ray emission in the detection elements 7.

The purpose (1) is expected to be achieved in the above described manner. As for the purpose (2), if the radiographic apparatus 1 takes a long time to detect a start of X-ray emission from the X-ray generator, the X-ray emission ends soon after the radiographic apparatus 1 detects the emission start and enters the charge accumulating state (or the X-ray emission has already ended), and the charge generated in the detection elements 7 through the X-ray emission can hardly be accumulated in the detection elements 7. As a result, an appropriate radiological image cannot be generated based on image data D read from the detection elements 7.

With the above two purposes (1) and (2) being taken into consideration, the predetermined time $\Delta T$ and the predetermined number N described above are set. In a case where the purpose (1) to prevent wrong detection of a start of emission due to natural radiation is taken into consideration, if the masking time $\Delta tm$ is set as described above, and the radiation that has reached the radiation sensor 25 is natural radiation, the probability that natural radiation again reaches the radiation sensor 25 within the predetermined time $\Delta T$ since natural radiation first reached the radiation sensor 25 and the radiation sensor 25 started outputting the pulse signal P is very low. Therefore, unless the predetermined time $\Delta T$ is longer than necessary, the possibility that the pulse signal P is again output from the radiation sensor 25 within the predetermined time T since natural radiation first reached the radiation sensor 25 and the radiation sensor 25 started outputting the pulse signal P is low.

If the radiation that has reached the radiation sensor 25 is X-rays, on the other hand, the probability that X-rays again reach the radiation sensor 25 within the predetermined time $\Delta T$ since X-rays first reached the radiation sensor 25 and the radiation sensor 25 started outputting the pulse signal P is high, and the possibility that the pulse signal P is output from the radiation sensor 25 a number of times within the predetermined time $\Delta T$ since X-rays first reached the radiation sensor 25 and the radiation sensor started outputting the pulse signal P is high.

Therefore, in a case where the above purpose (1) is taken into consideration, when the predetermined number N is made larger, wrong detection of a start of emission due to natural radiation can be prevented more accurately. Where the predetermined number N is made larger or is set at three, for example, a start of X-ray emission from the X-ray generator can be detected when the pulse signal P is output for the third time since the radiation sensor 25 started outputting the pulse signal P. However, where the predetermined number N is increased to four, a start of X-ray emission from the X-ray generator is detected for the first time when the pulse signal P is output for the fourth time since the radiation sensor 25 started outputting the pulse signal P, and a longer time is required to detect the start of the X-ray emission since the X-ray emission from the X-ray generator actually started.

That is, where the predetermined number N is made larger, wrong detection of a start of X-ray emission due to natural radiation can be prevented more accurately, but the radiographic apparatus 1 requires a longer time to detect a start of X-ray emission since the X-ray emission from the X-ray generator actually started.

So as to shorten the time required by the radiographic apparatus 1 to detect a start of X-ray emission since the X-ray emission from the X-ray generator actually started, the predetermined number N needs to be made smaller, though the probability that a start of X-ray emission due to natural radiation is wrongly detected becomes higher.

As described above, the above purposes (1) and (2), or (1) to prevent wrong detection of a start of X-ray emission due to natural radiation and (2) to promptly detect a start of X-ray emission from the X-ray generator, is in a so-called trade-off relation. The predetermined time $\Delta T$ is made longer as the predetermined number N is made larger.

In view of this, the irradiation start detecting unit 22 can be designed to simultaneously perform detection processes using different predetermined times $\Delta T$ and different predetermined numbers N, and detect a start of X-ray emission from the X-ray generator when determining that X-ray emission from the X-ray generator has started in one of the detection processes.

This structure can be applied not only in a case where the radiographic apparatus 1 includes two or more radiation sensors 25 as in this embodiment, but also in a case where the radiographic apparatus 1 includes only one radiation sensor 25. For example, a first detection process in which the predetermined time $\Delta T$ is set at $\Delta T1$ and the predetermined number N is set at three, and a second detection process in which the predetermined time $\Delta T$ is set at $\Delta T2$, which is longer than $\Delta T1$, and the predetermined number N is set at four, can be simultaneously performed on the pulse signal P to be output from the single radiation sensor 25.

With this structure, a start of X-ray emission from the X-ray generator might be detected earlier by the first detection process with the predetermined number N set at three than by the second detection process with the predetermined number N set at four.

Figure 7:
FIG. 7 is a diagram for explaining a situation where a pulse signal is output from a radiation sensor at regular time intervals.

In a situation where the pulse signal P is output from the radiation sensor 25 at regular time intervals based on X-rays emitted from the X-ray generator as shown in FIG. 7, for example, a start of X-ray emission from the X-ray generator is detected earlier by the first detection process with the predetermined number N set at three than by the second detection process with the predetermined number N set at four.

However, as mentioned above, even if X-rays are emitted from the X-ray generator at a fixed dose rate, the phenomenon that the photons that constitute the X-rays reach the radiation sensor 25 is a probabilistic phenomenon. Therefore, the pulse signal P is not necessarily output from the radiation sensor 25 at regular time intervals as shown in FIG. 7.

Figure 8:
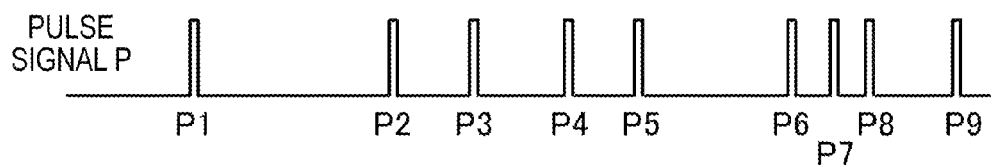
FIG. 8 is a diagram showing an example of a pulse signal that is output from a radiation sensor.

In a case where the pulse signal P is output from the radiation sensor 25 in the manner shown in FIG. 8, for example, the irradiation start detecting unit 22 does not detect a start of X-ray emission from the X-ray generator through the first detection process with the predetermined number N set at three, unless the pulse signal P is output twice within the predetermined time $\Delta T1$ since a pulse signal P1 was output from the radiation sensor 25. Likewise, as for each of pulse signals P2 through P5, a start of X-ray emission is not detected unless the pulse signal P is output twice within the predetermined time $\Delta T1$ since each of the pulse signals P2 through P5 was output.

If pulse signals P7 and P8 are output within the predetermined time $\Delta T1$ since a pulse signal P6 was output from the radiation sensor 25, a start of X-ray emission from the X-ray generator is detected for the first time. That is, in this case, a start of X-ray emission from the X-ray generator is detected when the pulse signal P8 is output.

In the second detection process that has the predetermined number N set at four and is to be performed in parallel with the above described first detection process, the predetermined time $\Delta T2$ is set at a longer time than the predetermined time $\Delta T1$. When the three pulse signals P2, P3, and P4 are output within the predetermined time $\Delta T2$ since the pulse signal P1 was output from the radiation sensor 25, a start of X-ray emission from the X-ray generator is detected when the pulse signal P4 is output. That is, in this case, a start of X-ray emission from the X-ray generator is detected when the pulse signal P4 is output.

Accordingly, in this example, a start of X-ray emission from the X-ray generator is detected earlier by the second detection process with the predetermined number N set at four than by the first detection process with the predetermined number N set at three. As a result of performing the two detection processes in parallel, the irradiation start detecting unit 22 detects a start of X-ray emission from the X-ray generator when the pulse signal P4 is output.

As described above, as in Modification 1, a start of X-ray emission from the X-ray generator is not necessarily detected earlier by a detection process with the predetermined number N set at a smaller number than by another detection process with the predetermined number N set at a larger number.

Where the irradiation start detecting unit 22 is designed to simultaneously perform detection processes that have different predetermined times $\Delta T$ and different predetermined numbers N, and detect a start of X-ray emission from the X-ray generator when determining that a start of X-ray emission from the X-ray generator is detected by one of the detection processes, a start of X-ray emission from the X-ray generator can be precisely detected while both of the above purposes (1) and (2) are satisfied: (1) to prevent wrong detection of a start of X-ray emission due to natural radiation; and (2) to promptly detect a start of X-ray emission from the X-ray generator.

Not only Modification 1 but also each of the modifications described below can achieve the above described effect to enable accurate detection of a start of X-ray emission from the X-ray generator while satisfying the above purposes: (1) to prevent wrong detection of a start of X-ray emission due to natural radiation; and (2) to promptly detect a start of X-ray emission from the X-ray generator.

[Modification 2-1]

In Modification 1 described above, the irradiation start detecting unit 22 simultaneously performs detection processes having different predetermined times $\Delta T$ and different predetermined numbers N based on the pulse signal P (see FIG. 8, for example) that is output from only one radiation sensor 25. However, Modification 1 described above can be applied in a case where two or more radiation sensors 25 are used.

In this case, each of the radiation sensors 25 can be designed to simultaneously perform detection processes having different predetermined times $\Delta T$ and different predetermined numbers N based on the pulse signal P output from the radiation sensor 25. Specifically, in a case where three radiation sensors 25 are provided, for example, and each of the radiation sensors 25 is designed to perform two kinds of detection processes (the above described first and second detection processes, for example), the two kinds of detection processes are performed in parallel on the pulse signal P that is output from each radiation sensor 25. Accordingly, a total of 3×2=6 types of detection processes are performed in parallel. When X-ray emission from the X-ray generator is determined have started in one of those detection processes, a start of X-ray emission from the X-ray generator is detected.

[Modification 2-2]

Alternatively, two or more radiation sensors 25 can be designed to simultaneously perform detection processes having different predetermined times $\Delta T$ and different predetermined numbers N. Specifically, a first radiation sensor 25 can be designed to perform a detection process having the predetermined number N set at three, and a second radiation sensor 25 can be designed to perform a detection process having the predetermined number N set at four, for example.

It is also possible to combine Modifications 2-1 and 2-2 in performing the process of detecting a start of X-ray emission from the X-ray generator.

[Modification 3]

Two or more radiation sensors 25 are used, as in Modifications 2-1 and 2-2 described above. However, detection processes with the same predetermined time $\Delta T$ and the same predetermined number N may be performed in parallel on the respective radiation sensors 25.

[Modification 4]

In a case where radiation sensors 25 are used, the irradiation start detecting unit 22 may be designed to perform an OR operation on pulse signals P that are output from two or more of the radiation sensors 25, and detect a start of X-ray emission from the X-ray generator when the ORed pulse signal $P_+$ is output the predetermined number N of times within the predetermined time $\Delta T$ in the same manner as above. This will be described below in detail.

Figure 9A:
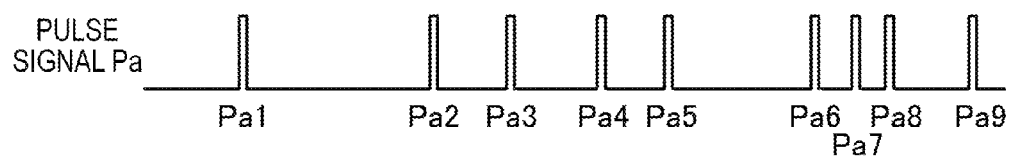
FIGS. 9A and 9B are diagrams showing examples of pulse signals that are output from respective radiation sensors.
Figure 9B:
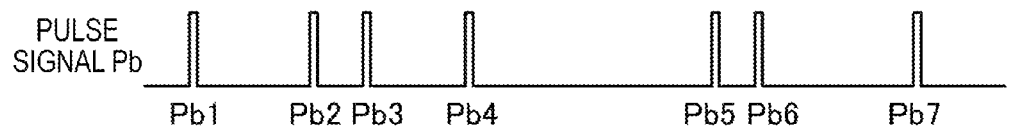
Figure 9C:
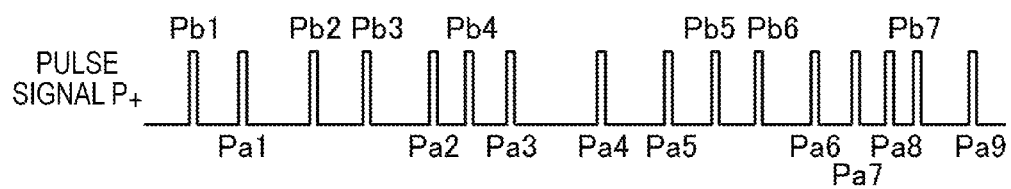
FIG. 9C is a diagram showing a pulse signal obtained by performing an OR operation on the pulse signals shown in FIGS. 9A and 9B.

In a case where pulse signals Pa and Pb are output from two radiation sensors 25A and 25B as shown in FIGS. 9A and 9B, for example, an OR operation is performed on these pulse signals Pa and Pb, to obtain the pulse signal $P_+$ shown in FIG. 9C. The pulse signal Pa shown in FIG. 9A is output at the same timing as the timing to output the pulse signal P shown in FIG. 8.

As in the example case shown in FIG. 8, the same predetermined time $\Delta T1$ as above is set as the predetermined time $\Delta T$ for the pulse signal Pa (see FIG. 9A) to be output from the radiation sensor 25A. If the predetermined number N is set at three, a start of X-ray emission is not detected with respect to pulse signals Pa1 through Pa5 output from the radiation sensor 25A in a detection process based on the pulse signal Pa output from the radiation sensor 25A. When pulse signals Pa1 and Pa8 are output within the predetermined time $\Delta T1$ since a pulse signal Pa6 was output from the radiation sensor 25A, a start of X-ray emission from the X-ray generator is detected for the first time. That is, in this case, a start of X-ray emission from the X-ray generator is detected when the pulse signal Pa8 is output.

The predetermined time $\Delta T1$ is also set for the pulse signal Pb to be output from the radiation sensor 25B, and the predetermined number N is set at three as described above. In a case where the pulse signal Pb is output from the radiation sensor 25B as shown in FIG. 9B, a start of X-ray emission is not detected with respect to any of pulse signals Pb1 through Pb7 that are output from the radiation sensor 25B. That is, within the time range shown in FIG. 9B, the pulse signal Pb is not output twice within the predetermined time $\Delta T1$ since the radiation sensor 25B started outputting the pulse signal Pb, and therefore, a start of X-ray emission from the X-ray generator is not detected in the detection process based on the pulse signal Pb that is output from the radiation sensor 25B.

Meanwhile, the longer predetermined time $\Delta T$ is set for the pulse signal $P_+$ (see FIG. 9C) obtained through an OR operation performed on the pulse signals Pa and Pb that have been output from the two radiation sensors 25A and 25B, and the predetermined number N is increased to four, for example. In this case, if three pulse signals Pa1, Pb2, and Pb3 are output within the predetermined time $\Delta T$ since the first ORed pulse signal Pb1 was output, a start of X-ray emission from the X-ray generator is detected.

That is, in the case of the detection process illustrated in FIGS. 9A through 9C, a start of X-ray emission from the X-ray generator is detected when the pulse signal Pb3 of the ORed pulse signal $P_+$ shown in FIG. 9C is output.

In the case of the above described structure, a start of X-ray emission from the X-ray generator is not necessarily detected earlier by the detection process based on the ORed pulse signal $P_+$ than by the detection process based on the pulse signal Pa or the pulse signal Pb detected from the radiation sensor 25A or the radiation sensor 25B.

Specifically, there are cases where X-rays are emitted onto a narrowed radiation field on the X-ray incidence surface R (see FIG. 2 and others) of the radiographic apparatus 1, and X-rays enter only one of two radiation sensors 25 while not entering the other one of the two radiation sensors 25, for example. In such a case, the pulse signal P is output from the one of the radiation sensors 25, but the pulse signal P is hardly output from the other one of the radiation sensors 25. Therefore, when the pulse signals P that are output from these two radiation sensors 25 are ORed, the ORed pulse signal $P_+$ is the same as the pulse signal P that is output from the one of the radiation sensors 25.

For each of the pulse signals P output from the two radiation sensors 25, the predetermined time $\Delta T$ is set, and the predetermined number N is set at three as described above. For the pulse signal P+ calculated through an OR operation, the predetermined time $\Delta T$ is made longer, and the predetermined number N is set at four, as described above. In such a case, a start of X-ray emission from the X-ray generator might be detected when the pulse signal P is output for the third time from one of the radiation sensors 25, for example, even before the pulse signal P is output for the fourth time (or before the ORed pulse signal $P_+$ is output for the fourth time).

As described above, even in the structure of Modification 4, a start of X-ray emission from the X-ray generator is not necessarily detected earlier by the detection process based on the ORed pulse signal $P_+$ than by the detection process based on the pulse signal P output from each of the radiation sensors 25.

The above structure of Modification 4 can achieve the effect of Modification 1, or more specifically, can achieve the effect to enable accurate detection of a start of X-ray emission from the X-ray generator while satisfying both of the above mentioned purposes: (1) to prevent wrong detection of a start of X-ray emission due to natural radiation; and (2) to promptly detect a start of X-ray emission from the X-ray generator.

[Modification 5]

Meanwhile, there are cases where radiographic imaging is performed through short-time X-ray emission from the X-ray generator at a high dose rate for a short time. In such a case, if the masking time $\Delta tm$ (see FIGS. 6A and 6B) is set in a detection process, a long time is required for the irradiation start detecting unit 22 of the radiographic apparatus 1 to detect a start of X-ray emission since the X-ray emission from the X-ray generator actually started, and a problem might be caused, as described in the above embodiment.

For example, the masking time $\Delta tm$ is set at 500 microseconds, and the predetermined number N is set at three in a detection process. For 500 microseconds after the pulse signal P is first output (or the ORed pulse signal P+ is output for the first time, which also applies in the description below), a check is not made to determine whether the pulse signal P has been output from the radiation sensor 25. When the 500 microseconds have passed, the pulse signal P is output for the second time. During 500 microseconds after the second output of the pulse signal P, a check is not made to determine whether the pulse signal P has been output from the radiation sensor 25. When the 500 microseconds have passed, the pulse signal P is output for the third time, and a start of X-ray emission is then detected.

Therefore, under the above described conditions for detection (the masking time $\Delta tm$ being 500 microseconds, the predetermined number N being three), at least one millisecond is required for the irradiation start detecting unit 22 to detect a start of X-ray emission, since X-ray emission from the X-ray generator actually started. In view of this, the control unit 22 of the radiographic apparatus 1 puts each of the TFTs 8 (see FIG. 5) into an off-state only after one millisecond has passed since X-ray emission from the X-ray generator actually started, and enters a charge accumulating state to accumulate the charge generated in the respective detection elements 7 through X-ray emission in the respective detection elements 7.

However, in a case where radiographic imaging is performed through short-time X-ray emission from the X-ray generator at a high dose rate for a short time as described above, X-ray emission has already ended when the radiographic apparatus 1 enters the charge accumulating state (or detects a start of X-ray emission), or X-ray emission might end immediately after the radiographic apparatus 1 enters the charge accumulating state. In such a situation, the charge generated in the respective detection elements 7 through X-ray emission is not or hardly accumulated in the respective detection elements 7, and therefore, radiographic imaging cannot be accurately performed.

In Modification 5, so as to cope with the above situation or a situation where radiographic imaging is performed through short-time X-ray emission from the X-ray generator at a high dose rate, the detection process described below may be performed in parallel with a detection process according to the above described embodiment or any of the above described modifications, for example.

Specifically, the predetermined masking time $\Delta tm$ described above is not set, and it is possible to perform a process of detecting a start of X-ray emission from the X-ray generator when the pulse width W or the total of the numbers M of the pulse signals P (or the pulse signals $P_+$; the same applies in the description below) that are output within a predetermined period $\Delta \tau$ since one or more radiation sensors 25 started outputting the pulse signal P, or the pulse signal $P_+$ obtained through an OR operation performed on the pulse signals P output from the respective sensors 25 was output for the first time, is equal to or greater than a threshold value, for example.

This is now described in detail. In a case where the masking time $\Delta tm$ is not set as described above, wrong detection of a start of X-ray emission due to natural radiation should also be avoided. In a case where the energy of natural radiation that has entered the radiation sensor 25 is small, the voltage value Va at the radiation sensor 25 changes as indicated by B or C in FIG. 3, for example, and the pulse signal P is output once, or twice at the most, every time natural radiation enters the radiation sensor 25 once.

If the energy of natural radiation that has entered the radiation sensor 25 is large, on the other hand, the voltage value Va at the radiation sensor 25 changes greatly as indicated by A in FIG. 3, for example, and the pulse signal P is output more than once every time natural radiation enters the radiation sensor 25 once. However, even if the energy of natural radiation is large, the pulse signal P is not output from the radiation sensor 25 unless the next natural radiation enters the radiation sensor 25 after the pulse signal P is output more than once in response to natural radiation that has entered the radiation sensor 25.

Figure 10A:
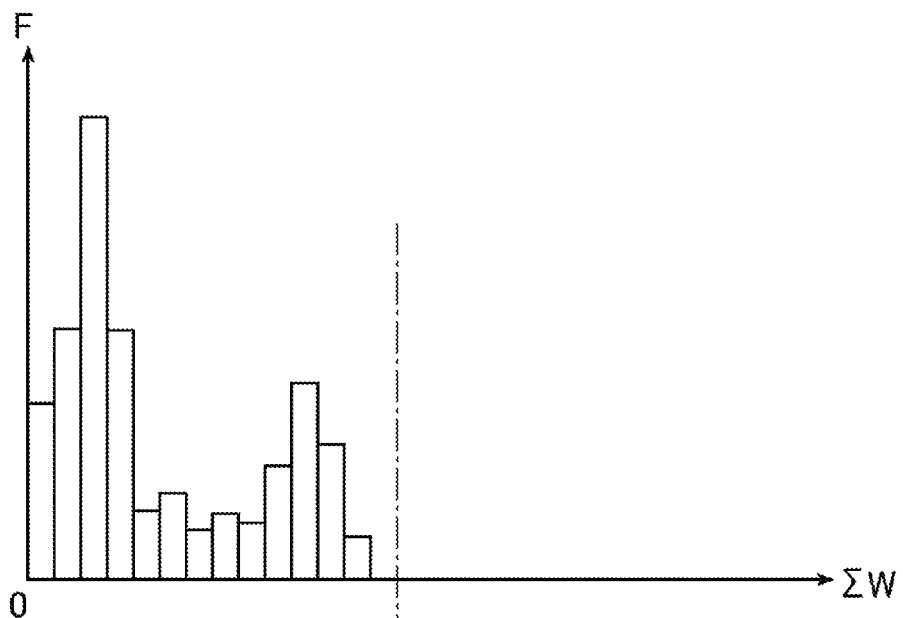
FIG. 10A is a diagram showing a distribution of the totals of the pulse widths of pulse signals that are output in a case where natural radiation enters a radiation sensor.

In view of this, X-rays are not emitted to the radiographic apparatus 1, and a total $\Sigma W$ of the pulse widths W (or the periods during which the pulse signal P is ON in FIG. 3, for example) of the pulse signals P that are output from the radiation sensor 25 during the predetermined period $\Delta \tau$ is calculated, and the total $\Sigma W$ is cast in a histogram. In a case where the radiation that enters the radiation sensor 25 is natural radiation, the distribution of the total values $\Sigma W$ of the pulse widths W falls within a range below the maximum value, as shown in FIG. 10A, for example. This became apparent from experiments and the like conducted by the inventors.

In the distribution shown in FIG. 10A, the small peak close to the maximum value is formed by cosmic rays or the like having large energy. In each of FIGS. 10A and 10B, the ordinate axis F indicates frequency.

In a case where X-rays are emitted from the X-ray generator to the radiographic apparatus 1, on the other hand, the radiation sensor 25 characteristically continues to output the pulse signal P, as long as X-rays are emitted to the radiographic apparatus 1. In a case where X-rays are emitted at a high dose rate from the X-ray generator as described above, the frequency at which X-rays enter the radiation sensor 25 becomes higher than that in a case where X-rays are emitted at a lower dose rate. That is, as the dose rate of X-rays emitted from the X-ray generator becomes higher, the frequency at which the pulse signal P is output from the radiation sensor 25 normally becomes higher, and the number of pulse signals P that are output from the radiation sensor 25 within the predetermined period $\Delta \tau$ becomes larger.

Figure 10B:
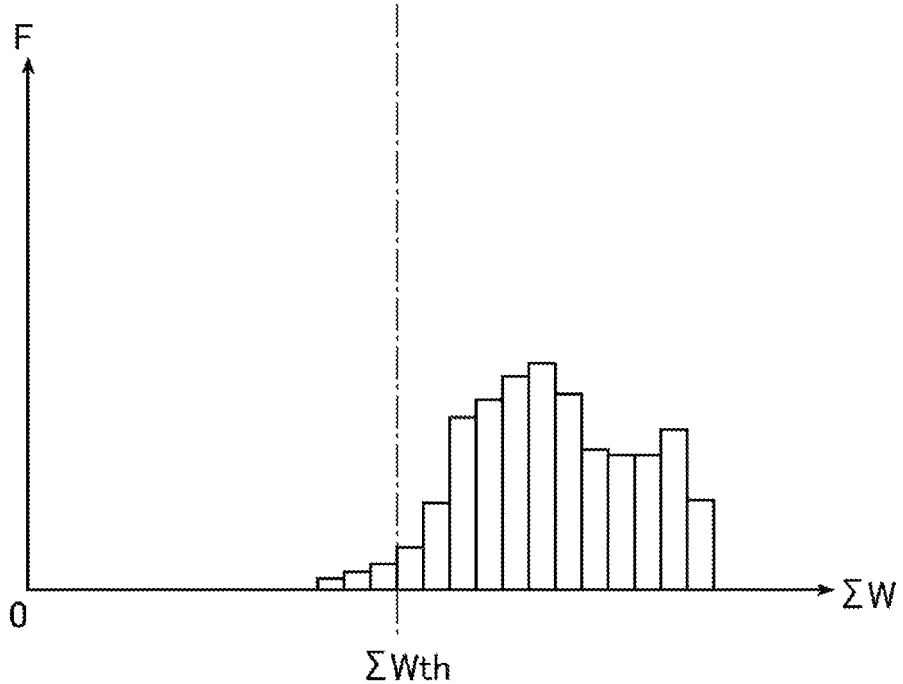
FIG. 10B is a diagram showing a distribution of the totals of the pulse widths of pulse signals that are output in a case where X-rays with a high dose rate enter a radiation sensor.

Therefore, in a case where the total $\Sigma W$ of the pulse widths W of the pulse signals P output from the radiation sensor 25 within the predetermined period $\Delta \tau$ is calculated and is cast in a histogram in the same manner as above, the distribution of the total values $\Sigma W$ of the pulse widths W shifts to the larger side (or to the right side in the histogram shown in FIG. 10B) when X-rays are emitted at a high dose rate from the X-ray generator, as shown in FIG. 10B. This became apparent from experiments and the like conducted by the inventors.

As the dose rate of X-rays emitted from the X-ray generator becomes higher, this distribution shifts further to the right in the histogram shown in FIG. 10B. As the predetermined period $\Delta \tau$ is made longer, this distribution shifts further to the right in the histogram shown in FIG. 10B. As can be seen from the histograms in FIGS. 10A and 10B, if an appropriate threshold value $\Sigma Wth$ is set, a check can be accurately made to determine whether the radiation that has entered the radiation sensor 25 is natural radiation (the case shown in FIG. 10A), or whether the radiation that has entered the radiation sensor 25 is X-rays emitted from the X-ray generator (the case shown in FIG. 10B).

In view of this, the irradiation start detecting unit 22 of the radiographic apparatus 1 calculates the total $\Sigma W$ of the pulse widths W of the pulse signals P (or the pulse signals $P_+$) that are output within the predetermined period $\Delta \tau$ since the one or more radiation sensors 25 started outputting the pulse signal P or the pulse signal $P_+$ calculated through an OR operation performed on the pulse signals P output from the respective radiation sensors 25 was output for the first time, without setting the predetermined masking time $\Delta tm$, as described above. When the total $\Sigma W$ of the pulse widths W becomes equal to or greater than the threshold value $\Sigma Wth$, the irradiation start detecting unit 22 detects a start of X-ray emission from the X-ray generator.

In a case where the radiation that has entered the radiation sensor 25 is natural radiation, the radiation sensor 25 may output the pulse signal P more than once as indicated by A in FIG. 3, or may output the pulse signal P only once as indicated by B and C in FIG. 3. The probability that natural radiation enters the radiation sensor 25 within the predetermined period $\Delta \tau$ is normally very low.

Therefore, if the radiation that has entered the radiation sensor 25 is natural radiation, only a few pulse signals P (or pulse signals $P_+$; the same applies in the description below) are output within the predetermined period $\Delta \tau$ since the one or more radiation sensors 25 started outputting the pulse signal P or the pulse signal $P_+$ calculated through an OR operation performed on the pulse signals P output from the respective radiation sensors 25 was output for the first time.

In a case where the radiation that has entered the radiation sensor 25 is X-rays emitted from the X-ray generator, on the other hand, the number M of pulse signals P that are output from the radiation sensor 25 per unit time becomes larger, as the dose rate of the X-rays emitted from the X-ray generator becomes higher. The number M of pulse signals P that are output from the radiation sensor 25 continues to increase, as long as X-rays are emitted from the X-ray generator, as in the above described case.

Therefore, although not shown in the drawing, if an appropriate threshold value ΣMth with respect to the total ΣM of the numbers M of pulse signals P that are output from the radiation sensor 25 is set, a check can be accurately made to determine whether the radiation that has entered the radiation sensor 25 is natural radiation, or whether the radiation that has entered the radiation sensor 25 is X-rays emitted from the X-ray generator, as in the above described case.

In view of this, the irradiation start detecting unit 22 of the radiographic apparatus 1 counts the total ΣM of the numbers M of the pulse signals P (or the pulse signals P+) that are output within the predetermined period Δτ since the one or more radiation sensors 25 started outputting the pulse signal P or the pulse signal P+ calculated through an OR operation performed on pulse signals P output from the respective radiation sensors 25, without setting the predetermined masking time Δtm, as described above. When the total ΣM of the numbers M becomes equal to or greater than the threshold value ΣMth, the irradiation start detecting unit 22 detects a start of X-ray emission from the X-ray generator.

If a long period is set as the predetermined period Δτ, the irradiation start detecting unit 22 of the radiographic apparatus 1 takes a long time to detect a start of X-ray emission since X-ray emission from the X-ray generator actually started, and the same problem as above is caused. Therefore, the predetermined period Δτ is made as short as possible, so that a check can be accurately made to determine whether the radiation that has entered the radiation sensor 25 is natural radiation, or whether the radiation that has entered the radiation sensor 25 is X-rays emitted from the X-ray generator.

As the dose rate of X-rays emitted from the X-ray generator becomes higher, the frequency at which the pulse signal P is output from the radiation sensor 25 becomes higher, as described above. Accordingly, the predetermined period Δτ can be made even shorter in such a case. In view of this, the predetermined period Δτ can be changed in accordance with the dose rate that is set in the X-ray generator (or the tube voltage or the tube current that is set for defining the dose rate, for example).

It is possible to combine Modifications 1 through 5, as well as modifications other than the above described ones, in performing a process of detecting a start of X-ray emission from the X-ray generator, and the detection method is determined as appropriate.

[Collection of Data Related to Natural Radiation]

In a case where the radiographic apparatus 1 is used for radiographic imaging in an environment with a large amount of natural radiation, for example, the frequency that natural radiation enters the radiation sensor 25 might become higher than normal. Further, the distribution in Modification 5 shown in FIG. 10A (or the distribution of the totals ΣW of the pulse widths W of the pulse signals P that are output from the radiation sensor 25 within the predetermined period Δτ in a case where the radiation entering the radiation sensor 25 is natural radiation) might shift further to the right in the histogram shown in FIG. 10A. Therefore, in a case where the radiographic apparatus 1 is used in an environment with a large amount of natural radiation, a start of X-ray emission is wrongly detected more often due to natural radiation.

In a case where the radiographic apparatus 1 is used in an environment with a large amount of natural radiation in the above described embodiment, instead of Modification 5 described above, the probability that the number of times the pulse signal P is output in response to natural radiation entering the radiation sensor 25 reaches the predetermined number N before the predetermined time T has passed since the natural radiation entered the radiation sensor 25, though X-rays are not being emitted from the X-ray generator, becomes higher than normal. Therefore, in a case where the radiographic apparatus 1 is used in an environment with a large amount of natural radiation in the above described embodiment, a start of X-ray emission is wrongly detected more often due to natural radiation.

Therefore, a service person can visit the site where the radiographic apparatus 1 is being used, and measure how often natural radiation enters the radiation sensor 25 of the radiographic apparatus 1 (or determine whether there are many natural radiant rays in the environment). However, the number of rays that enter the radiation sensor 25 during the short visit by the service person is small. Therefore, even if the number of natural radiant rays that enter the radiation sensor 25 per unit time is calculated the service person, the error in the calculation is very large. For this reason, it is difficult, in many cases, to determine whether the environment in which the radiographic apparatus 1 is being used is an environment with a large amount of natural radiation, or whether the radiographic apparatus 1 often wrongly detects a start of X-ray radiation due to natural radiation in the environment.

In view of this, the irradiation start detecting unit 22 (or the control unit 22 or the like) of the radiographic apparatus 1 collects information about the pulse signals P that were output while X-rays were not emitted from the X-ray generator. The irradiation start detecting unit 22 also collects information about the time during which the information about the pulse signals P was collected. The information is then stored into a memory such as the storage unit 23 (see FIG. 5) or a ROM.

In this case, the irradiation start detecting unit 22 of the radiographic apparatus 1 can collect the information when performing the process of detecting a start of X-ray emission from the X-ray generator as described in the above embodiment or in each of the modifications.

While the information is collected, the pulse signals P that are output from the radiation sensor 25 during the period from the start of the detection process to the detection of a start of X-rays by the irradiation start detecting unit 22 are regarded as pulse signals P generated from natural radiation. However, the irradiation start detecting unit 22 does not necessarily detect a start of X-ray emission immediate after X-ray emission from the X-ray generator is started, as shown in FIG. 8. That is, a start of X-ray emission might be detected for the first time only after X-rays emitted from the X-ray generator have reached the radiation sensor 25 and the pulse signal P has already been output a few times (or when the pulse signal P8 is output in the example shown in FIG. 8).

In such a case, if the pulse signals P1 through P7 shown in FIG. 8 (or the pulse signals P1 through P5, excluding the pulse signals P6 through P8 used in the detection) are counted as pulse signals P generated from natural radiation, a check cannot be accurately made to determine whether the environment in which the radiographic apparatus 1 is being used is an environment with a large amount of natural radiation.

Therefore, while the information is collected, the pulse signals P that are output from the radiation sensor 25 during the period from the start of the detection process by the irradiation start detecting unit 22 to a predetermined time (one second, for example) before the detection of a start of X-ray emission are regarded as pulse signals generated from natural radiation. In practice, the irradiation start detecting unit 22 requires less than one second to detect a start of X-ray emission from the X-ray generator since the X-ray emission from the X-ray generator actually started. In view of this, at least the pulse signals P that are output during the period from the start of the detection process by the irradiation start detecting unit 22 to one second before the detection of a start of X-ray emission from the X-ray generator can be regarded as pulse signals generated from natural radiation.

The information is not necessarily collected when the above described detection process is performed, as long as it is possible to collect the information about the pulse signals P that are output from the radiation sensor 25 while X-rays are not being emitted from the X-ray generator, and the information about the time during which the information about the pulse signals P was collected. For example, the radiation sensor 25 and others may be automatically activated at a certain time of the day during which X-rays are not generated from the X-ray generator, so that the information about pulse signals P is collected every day.

The information about the pulse signals P and the information about the time during which the information about pulse signals P was collected may be minute information, such as the date on which the information was collected, the time of the start and the time of the end of the information collection, the times when the pulse signals P were output from the radiation sensor 25, and the pulse widths W. It is also possible to collect and save only the information about the duration of time during which the information was collected, and the information about the number of the pulse signals P that were output from the radiation sensor 25 during the information collecting time. In that case, the information about the pulse signals P and the information about the time during which the information about the pulse signals P was collected are handled as appropriate.

In a case where the radiographic apparatus 1 is used in an environment with a large amount of natural radiation, a start of X-ray emission due to natural radiation is wrongly detected more often than in a case where the radiographic apparatus 1 is used in an environment with a small amount of natural radiation. If the predetermined number N is set at a larger number in a case where the detection process according to the above described embodiment is performed, a start of X-ray emission due to natural radiation is wrongly detected less often. In such a case, the predetermined time ΔT should also be made longer.

In a case where the environment is determined to be an environment with a large amount of natural radiation based on the information about the pulse signals P and the like collected and saved in the above described manner, the predetermined period ΔT can be made longer and the predetermined number N can be made larger. This determination may be conducted by the radiographic apparatus 1. Alternatively, the determination may be conducted by an external device, and, in accordance with an instruction from the external device, the irradiation start detecting unit 22 of the radiographic apparatus 1 may change the predetermined time T and the predetermined number N.

In Modification 5 described above, if X-rays are not emitted to the radiographic apparatus 1 over a long time in an environment with a large amount of natural radiation, the number of the pulse signals P that are output from the radiation sensor 25 within the predetermined period Δτ becomes larger than that in an environment with a small amount of natural radiation. Therefore, when the total ΣW of the pulse widths W of the pulse signals P is calculated and cast in the histogram in the same manner as above, the distribution of the totals ΣW might be expanded toward the larger side (or to the right side in the histogram in FIG. 10A), compared with the distribution shown in FIG. 10A.

In a case where the distribution of the totals ΣW is expanded toward the larger side, the threshold value ΣWth needs to be changed to a greater value. The same applies to the total of the numbers M (described in Modification 5) of the pulse signals P that are output within the predetermined period Δτ. In an environment with a large amount of natural radiation, the threshold value for the total of the numbers M of the pulse signals P that are output within the predetermined period Δτ needs to be changed to a larger value in the same manner as above.

In a case where the detection process according to Modification 5 is employed, for example, if the environment is determined to be an environment with a large amount of natural radiation, the threshold value ΣWth can also be changed to a larger value.

In a case where the predetermined time T and the predetermined number N are not changed, or where the threshold value ΣWth or the like is not changed (or cannot be changed) in the above manner, if the environment is determined to be an environment with a large amount of natural radiation based on the information about the pulse signals P and the like as described above, for example, the user of the radiographic apparatus 1 can be notified that wrong detection often occurs in the environment (or that the detection ability in the process of detecting a start of X-ray emission is low in the environment).

In this case, the radiographic apparatus 1 can display the notification on a display unit thereof (not shown) or issue the notification through sound. Alternatively, the notification may be issued by an external device.

In conjunction with a detection process according to the present invention (or the detection process according to the above embodiment or any of the detection processes described above as the modifications), a detection process disclosed in JP 2009-219538 A may be performed to detect a start of X-ray emission based on the current flowing through the bias lines 9 (see FIG. 5), a detection process disclosed in WO 2011/135917 A may be performed to detect a start of X-ray emission based on leak data "d leak" obtained by the readout circuit 17 reading the charge leaking from the detection elements 7 via the TFTs 8 in an off-state, or a detection process disclosed in WO 2011/152093 A may be performed to detect a start of X-ray emission based on image data read out through an image data readout process performed prior to imaging, for example.

In a case where the environment is determined to be an environment with a large amount of natural radiation based on the collected and saved information about the pulse signals P and the like as described above, a detection process according to the present invention is stopped (or any detection process according to the present invention is not performed), and a detection process disclosed in one of the above publications may be performed to detect a start of X-ray emission from the X-ray generator.

If the radiographic apparatus 1 is moved to a different site and is used in an environment with a small amount of natural radiation, the detection process according to the present invention is resumed, and the detection process according to the present invention is independently performed or is performed in conjunction with a detection process disclosed in one of the above publications, to detect a start of X-ray emission from the X-ray generator.

In the embodiment and the respective modifications described above, the pulse signal P is output from the radiation sensor(s) 25. However, the analog voltage value Va (see FIG. 3) as a signal value may be output from the radiation sensor 25 to the irradiation start detecting unit 22, as described above. In that case, the pulse signal P being output from the radiation sensor 25 in the above embodiment and the respective modifications is equivalent to the voltage value Va being outside a predetermined range. Accordingly, in a case where the analog voltage value Va as a signal value is output from the radiation sensor 25, the present invention can be applied in the same manner as in the case where the pulse signal P is output from the radiation sensor 25.

Although the present invention has been described and illustrated in detail, it is clearly understood that the same is by way of illustrated and example only and is not to be taken by way of limitation, the scope of the present invention being interpreted by terms of the appended claims.

What is claimed is:

1. A radiographic apparatus comprising:
a plurality of detection elements arranged in a two-dimensional fashion;
at least one radiation sensor configured to change a signal value to be output, when radiation is emitted thereto; and
an irradiation start detecting unit configured to determine whether X-ray emission from an X-ray generator has been started based on the signal value output from the radiation sensor,
wherein,
when the number of times the signal value output from the radiation sensor moves out of the predetermined range within a predetermined time since the signal value output from the radiation sensor first moved out of the predetermined range reaches a predetermined plurality of times, the irradiation start detecting unit detects a start of X-ray emission from the X-ray generator; and
wherein the irradiation start detecting unit is configured such that the number of times the signal value output from the radiation sensor moves out of the predetermined range is not counted until a predetermined masking time has passed since the signal value moved out of the predetermined range.

2. The radiographic apparatus according to claim 1, wherein the irradiation start detecting unit performs a plurality of detection processes that differ in the predetermined time and the predetermine number, and, when determining that X-ray emission from the X-ray generator has started through one of the detection processes, detects a start of X-ray emission from the X-ray generator.

3. The radiographic apparatus according to claim 1, wherein
the at least one radiation sensor is formed with a plurality of radiation sensors, and
the irradiation start detecting unit performs detection processes in parallel based on the respective signal values output from the radiation sensors, and, when determining that X-ray emission from the X-ray generator has started through the detection process based on the signal value output from one of the radiation sensors, detects a start of X-ray emission from the X-ray generator.

4. The radiographic apparatus according to claim 1, wherein the radiation sensor outputs a pulse signal when the signal value moves out of the predetermined range,
the irradiation start detecting unit does not determine whether the pulse signal has been output from the radiation sensor at least until the predetermined masking time has passed since the pulse signal was output from the radiation sensor, and
when the number of times the pulse signal is output from the radiation sensor within a predetermined time since the pulse signal was output from the radiation sensor for the first time meets a predetermined threshold, the irradiation start detecting unit detects a start of X-ray emission from the X-ray generator.

5. The radiographic apparatus according to claim 4, wherein
the at least one radiation sensor is formed with a plurality of radiation sensors,
the irradiation start detecting unit performs an OR operation on the pulse signals output from two or more of the radiation sensors, and
when the number of times the ORed pulse signal is generated within the predetermined time reaches a predetermined plurality of times, the irradiation start detecting unit detects a start of X-ray emission from the X-ray generator.

6. The radiographic apparatus according to claim 1, wherein the irradiation start detecting unit performs a detection process to detect a start of X-ray emission from the X-ray generator when a total of pulse widths or numbers of the pulse signals output within a predetermined period from the time when the radiation sensor started outputting the pulse signal to the time when the pulse signal calculated through an OR operation performed on the pulse signals output from two or more radiation sensors becomes equal to or larger than a threshold value, without setting the predetermined masking time.

7. The radiographic apparatus according to claim 4, wherein the irradiation start detecting unit collects information about the pulse signal output from the radiation sensor while X-rays are not emitted from the X-ray generator, and collects and saves information about a time during which the information about the pulse signal is collected.

8. The radiographic apparatus according to claim 7, wherein the predetermined time and the predetermined plurality of times are changed based on the information collected and saved.

9. A radiographic apparatus comprising:
a plurality of detection elements arranged in a two-dimensional fashion;
a radiation sensor configured to output a pulse signal when radiation is emitted thereto; and
a unit configured to collect information about whether the signal value output from the radiation sensor has exceeded the predetermined range for a predetermined plurality of times while X-rays are not being emitted from an X-ray generator, and collect and save information about a time during which the information about the pulse signal was collected;
wherein the unit is configured such that wherein the information about whether the signal value output from the radiation sensor has exceed the predetermined range is not collected unit a predetermined masking time has passed since the signal value moved out of the predetermined range.

* * * * *